United States Patent [19]

Hu

[11] Patent Number: 4,603,324
[45] Date of Patent: Jul. 29, 1986

[54] TONE-PIP-SIGNAL GENERATOR

[75] Inventor: Victor L. Hu, San Jose, Calif.

[73] Assignee: Minnesota Mining and Manufacturing Company, St. Paul, Minn.

[21] Appl. No.: 428,312

[22] Filed: Sep. 29, 1982

[51] Int. Cl.[4] .................. G08B 3/00; G08B 5/22; H03K 5/22
[52] U.S. Cl. .................. 340/384 E; 340/825.48; 307/236; 307/262
[58] Field of Search .......... 340/384 E, 825.48, 384 R; 331/47; 328/181, 184; 307/236, 262

[56] References Cited

U.S. PATENT DOCUMENTS

| | | | |
|---|---|---|---|
| 3,529,086 | 9/1970 | Atchison et al. | 340/384 E |
| 3,541,355 | 11/1970 | Kan | 307/236 |
| 4,090,349 | 5/1978 | Takase | 340/384 E X |
| 4,417,218 | 11/1983 | Berke | 328/184 X |

OTHER PUBLICATIONS

*Elektor*, vol. 5, No. 6, Jun. 1979, p. 6-12 to 6-16, "Programmable Doorbell".

Primary Examiner—John W. Caldwell, Sr.
Assistant Examiner—Tyrone Queen
Attorney, Agent, or Firm—Donald M. Sell; James A. Smith; William D. Bauer

[57] ABSTRACT

A tone-pip signal generator for use in systems employed in the identification and diagnosis of hearing defects, the generator including a counter for counting cycles of a clock signal which occur following the time marked by a reset signal, a gate circuit for coupling the clock signal to the counter until a predetermined count is accumulated, a memory addressed by the counter, the memory for retrieving in succession stored numbers representing respective time samples of the tone-pip signal and a digital-to-analog converter driven by the memory. Additionally, the generator includes an exclusive-OR-gate array for selectively inverting the tone-pip signal.

6 Claims, 2 Drawing Figures

TONE-PIP-SIGNAL GENERATOR

BACKGROUND OF THE INVENTION

1. Field of the Invention

The present invention relates to medical instruments generally and more particularly to a digital-type tone-pip-signal generator for an auditory-evoked-potential-measuring system.

2. Description of the Prior Art

Commonly, medical examination to identify and diagnose hearing defects includes observing the subjective response to auditory stimuli. The subjective sensitivity to stimuli level is measured at several auditory frequencies. Where such measurements are impractical, as, for example, of the very young, the evoked-action potentials resulting from the auditory stimulation may be measured.

Since the evoked-action potentials are often masked by other (EEG-type) brain-activity potentials, systems for measuring auditory-evoked potentials commonly employ a periodic stimulus. A periodic stimulus evokes a periodic potential which may be separated from the other more random potentials with a filter tuned to the periodic rate.

A stimulus commonly employed with auditory-evoked-potential measuring systems is that which is referred to as a tone pip. A tone pip includes a number of cycles of the auditory frequency the amplitude of which is defined by an envelope having an attack portion and a decay portion both chosen to minimize system ringing. A representative tone-pip signal is illustrated in FIG. 1 of the drawing generally designated by the number 10. The auditory cycles are designated by the number 12 and the attack and decay portions of the envelope are designated 14 and 16, respectively. (For clarity, the cycle period is shown expanded (distorted) with respect to the attack and decay periods.)

A prior-art-type generator for developing a tone-pip signal includes a linear-type sine-wave generator for developing a signal at the auditory frequency, a linear-type ramp generator for developing a signal representing the tone-pip envelope and a voltage-(gain) controlled amplifier for combining the signals to develop the tone-pip signal.

Unfortunately, it is difficult to develop a tone-pip signal of high accuracy with the above-mentioned prior-art-type generator. Additionally, improvements in signal accuracy are generally at the expense of circuit complexity.

SUMMARY OF THE PRESENT INVENTION

It is therefore a material object of the present invention to provide a generator for developing a highly accurate tone-pip signal.

Another object of the present invention is to provide a simple tone-pip-signal generator.

Briefly, a tone-pip-signal generator in accordance with the present invention includes a counter for counting cycles of a clock signal which occur following the time marked by a reset signal to develop signals representing the accumulated count and a gate circuit for coupling the clock signal to the counter until a predetermined count is accumulated. The generator also includes a memory storing numbers representing successive samples of the tone-pip signal, the memory being addressed by the counter developed signals to retrieve in succession the numbers representing the tone-pip signal. Additionally, the generator includes an exclusive-OR-gate array for inverting the signals developed by the memory to selectively invert the tone-pip signal and a digital-to-analog converter for developing the tone-pip signal from the memory developed signals.

An important advantage of the present invention is the accuracy of tone-pip signals which may be developed by generators in accordance therewith.

Other advantages of the present invention include the simplicity, economy and efficiency of generators in accordance therewith.

These and other objects and advantages of the present will no doubt become obvious to those of ordinary skill in the art after having read the following detailed description of the preferred embodiment illustrated in the drawing.

IN THE DRAWING

DESCRIPTION OF THE PREFERRED EMBODIMENT

Figure 1:
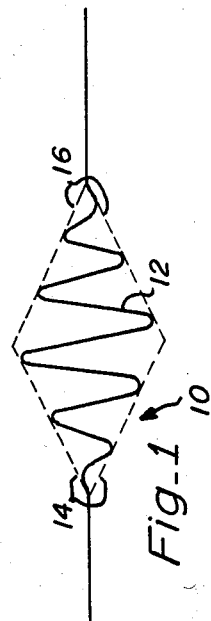
FIG. 1 is a representation of a tone-pip-signal.
Figure 2:
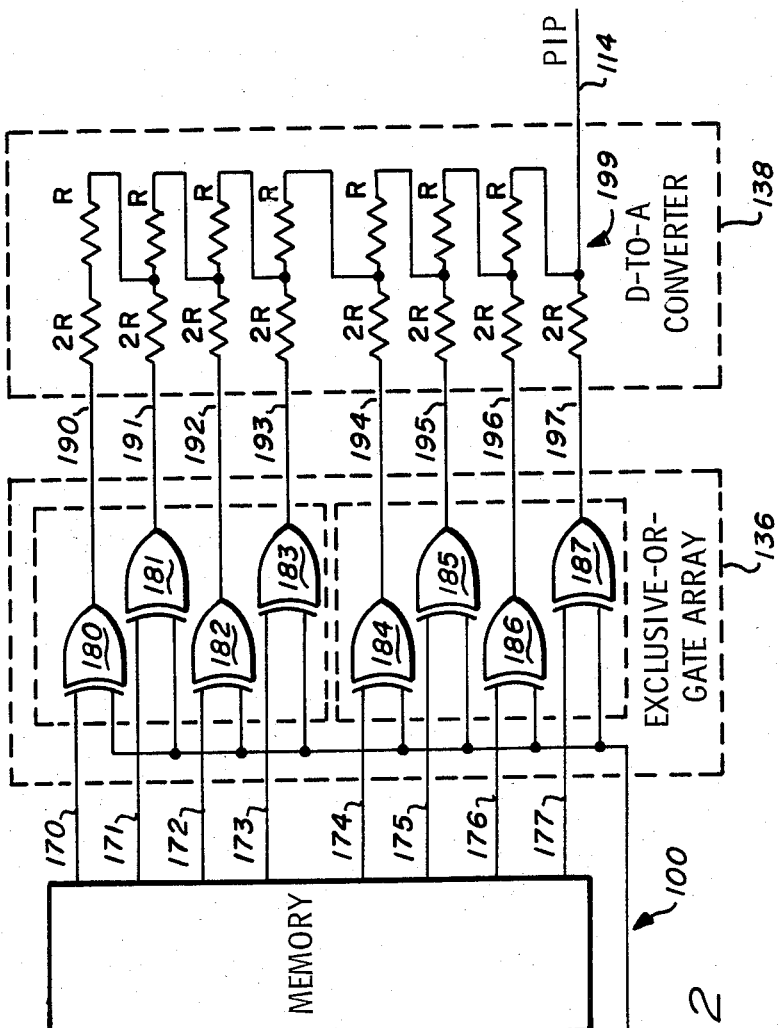
FIG. 2 is a schematic diagram of a tone-pip-signal generator in accordance with the present invention.
Figure 2:
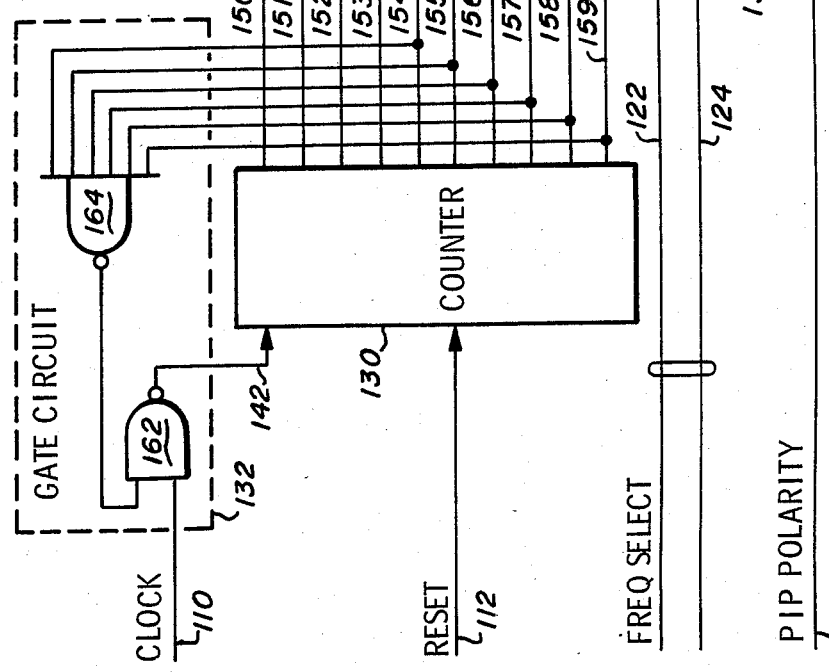

A preferred embodiment of a tone-pip-signal generator in accordance with the present invention is illustrated in FIG. 2 of the drawing generally designated by the number 100. Driven by a clock signal developed on a line 110, following each time marked by a reset signal developed on a line 112, generator 100 develops a tone-pip-signal on a line 114. The polarity of the tone-pip-signal developed on line 114 is controlled by a pip-polarity signal developed on a line 118; and the frequency of the signal is controlled by frequency selecting signals developed on a pair of lines designated 122 and 124.

Tone-pip-signal generator 100 includes as principal components a counter (divider) 130, a gate circuit 132, a memory 134, an exclusive-OR-gate array and a digital-to-analog (D-to-A) converter 138. In the preferred embodiment, counter 130 is of the ten-(or greater) stage ripple-carry binary type having a clock input connected to a line 142 for receiving the clock signal developed on line 110, a reset input connected to line 112 and ten (or more) output lines each connected to a respective one of ten lines designated 150 through 159, inclusive. Preferably, counter 130 includes a device of the type which is commonly designated 4040.

Counter 130 is reset responsive to a high-logic-level signal developed on line 112 and advanced responsive to each high-to-low transition of a logic-level signal developed on line 142. The counter develops logic-level signals on lines 150–159 which represent in digital format the count accumulated.

Gate circuit 132 includes two NAND gates designated 162 and 164. Gate 162 has an input connected to the output of gate 164, another input connected to line 110 and an output connected to line 142. Gate 164 also has six inputs each connected to a respective one of the lines 154–159, inclusive. Gate 162 couples (inverted) the clock signal developed on line 110 to line 142 until counter 130 reaches an accumulated count at which the counter develops high-logic-level signals on all of lines 154–159.

Memory 134 has 12 (or more) address inputs and 8 (or more) data outputs. Ten of the address inputs are connected to respective ones of the ten lines 150–159, inclusive, the remaining two address lines being connected to respective ones of the two lines 122 and 124. The eight data outputs are connected each to a respective one of eight lines designated 170 through 177, inclusive. Preferably, memory 130 includes a device of the erasable-programmable-read-only type (EPROM) and which is commonly designated 2732.

Memory 134 includes four portions each having 1024 locations each storing an eight-bit number, the four portions being defined by the address inputs connected to lines 122 and 124. The numbers stored in three of the four memory 134 portions represent respective time samples of the amplitude of respective tone-pip signals. Preferably, the three portions represent tone-pip signals the auditory frequency of which is a respective one of the three frequencies 500 hertz, 2000 hertz and 4000 hertz. The attack and decay periods of each tone-pip signal is 5 milliseconds. Thus, with a 100 kilohertz line 110 clock frequency, at least 25 time samples for each auditory frequency cycle is employed. The remaining memory 134 portion is employed to store time samples for developing a 40 hertz signal used for testing purposes.

Operationally, memory 134 develops on lines 170–177 signals which represent in digital format the numbers stored at the location which is addressed by the signals developed on lines 150–159, 122 and 124. Thus, as the count accumulated by counter 130 is successively advanced, successive locations in memory 134 are addressed causing memory 134 to develop on lines 170–177 signals which represent in digital format the tone-pip signal selected by the signals developed on lines 122 and 124.

Array 136 includes eight exclusive-OR gates designated 180–187, inclusive. Gates 180–187 each has an input connected to line 118, another input connected to a respective one of the eight lines 170–177, inclusive, and an output connected to a respective one of eight lines designated 190–197, inclusive. Preferably, array 136 includes a pair of devices of the type which are commonly designated 4030.

Each of gates 180–187 is operative to couple a respective one of the signals developed on lines 170–177 to a respective one of the lines 190–197. The signals are coupled in either inverted or non-inverted form responsive to the logic level of the pip-polarity signal developed on line 118.

Converter 138 develops the tone-pip signal on line 114 by converting from digital to analog format the signals developed on lines 190–197, inclusive. Preferably, converter 138 includes a resistor array of the R-2R type, the array being generally designated by the number 199.

While the invention has been particularly shown and described with reference to a preferred embodiment, it will be understood by those skilled in the art that there are alterations and modifications in form and detail that may be made therein. Accordingly, it is intended that the following claims cover all such alterations and modifications as fall within the true spirit and scope of the invention.

I claim:

1. A clock-signal-driven generator for developing a signal representing a tone pip of first predetermined frequency at each time marked by a reset signal, the generator comprising in combination:

counter means reset by the reset signal, said counter means for counting cycles of the clock signal and for developing a plurality of binary signals collectively representing the accumulated count;

gate means driven by at least one of said counter means developed signals, said gate means for coupling said clock signal to said counter means until a predetermined count is accumulated;

memory means driven by said counter means, said memory means having a first plurality of locations addressed at least in part by at least some of said counter means developed signals, each of said first plurality of memory locations storing a number representing a respective time sample of the amplitude of the tone-pip signal, said memory means for developing a plurality of binary signals collectively representing the addressed one of said numbers;

means for converting said memory means developed signals from digital to analog format to generate said tone-pip signal; and means for coupling said memory means developed signals to said digital-to-analog-converting means, wherein said coupling means includes a plurality of exclusive-OR gates each having an input for receiving a pip-signal-polarity-reversing signal, another input connected to said memory means to receive a respective one of said memory-means-developed signals and an output connected to said digital-to-anglaog-converting means.

2. A tone-pip-signal generator as recited in claim 1 wherein said gate means includes a first NAND gate having an output and a plurality of inputs each connected to said counter means to receive a predetermined one of said counter means developed signals and a second NAND gate having an input connected to said first NAND gate output, another input connected to receive said clock signal and an output connected to said counter means to selectively couple said clock signal thereto.

3. A tone-pip-signal generator as recited in claim 1 wherein said memory means further has a second plurality of locations addressed at least in part by said some of said counter means developed signals, each of said second plurality of locations storing a number representing a respective time sample of the amplitude of another tome-pip signal having a second predetermined frequency, said memory means being responsive to a frequency-selecting signal as an addressing signal for selecting between said first and said second plurality of memory locations.

4. A tone-pip-signal generator as recited in claim 3 wherein said gate means includes a first NAND gate having an output and a plurality of inputs each connected to said counter means to receive a predetermined one of said counter means developed signals and a second NAND gate having an input connected to said first NAND gate output, another input connected to receive said clock signal and an output connected to said counter means to selectively couple said clock signal thereto.

5. A tone-pip-signal generator as recited in claim 1 wherein said digital-to-analog-converting means includes an R-2R-type resistor array.

6. A tone-pip-signal generator as recited in claim 2 wherein said gate means couples said clock signal to said counter means until a predetermined non-zero count is accumulated.

* * * * *